(12) United States Patent
Kheraj

(10) Patent No.: US 11,882,407 B2
(45) Date of Patent: Jan. 23, 2024

(54) CHARGING CASE FOR EARBUDS

(71) Applicant: Reshma N Kheraj, Raleigh, NC (US)

(72) Inventor: Reshma N Kheraj, Raleigh, NC (US)

(*) Notice: Subject to any disclaimer, the term of this patent is extended or adjusted under 35 U.S.C. 154(b) by 472 days.

(21) Appl. No.: 17/223,338

(22) Filed: Apr. 6, 2021

(65) Prior Publication Data
US 2021/0250708 A1    Aug. 12, 2021

Related U.S. Application Data

(60) Provisional application No. 62/972,783, filed on Feb. 11, 2020.

(51) Int. Cl.
*H02J 7/00* (2006.01)
*H04R 25/00* (2006.01)
*A61L 2/10* (2006.01)

(52) U.S. Cl.
CPC ............. *H04R 25/602* (2013.01); *A61L 2/10* (2013.01); *H02J 7/0044* (2013.01); *A61L 2202/11* (2013.01); *H02J 2310/22* (2020.01); *H04R 2225/31* (2013.01)

(58) Field of Classification Search
USPC .................. 320/106, 107, 108, 109, 110
See application file for complete search history.

(56) References Cited

U.S. PATENT DOCUMENTS

| | | | | |
|---|---|---|---|---|
| 11,172,101 B1* | 11/2021 | Boozer | ................. | H04N 23/57 |
| 2016/0000953 A1* | 1/2016 | Bettles | ...................... | A61L 2/10 |
| | | | | 250/455.11 |
| 2017/0094399 A1* | 3/2017 | Chandramohan | ........ | H04R 9/06 |

FOREIGN PATENT DOCUMENTS

| | | | | |
|---|---|---|---|---|
| WO | WO-2017048877 A1 * | 3/2017 | ............... | A61L 2/10 |
| WO | WO-2019194344 A1 * | 10/2019 | ............. | A45C 11/00 |

* cited by examiner

*Primary Examiner* — Brian Ngo
(74) *Attorney, Agent, or Firm* — Barry Choobin; Patent 360

(57) ABSTRACT

A charging case having one or more charging docks for charging one or more earbuds. The charging case can further have UV LEDs for automatically sterilizing the earbuds while charging.

8 Claims, 2 Drawing Sheets

CHARGING CASE FOR EARBUDS

CROSS-REFERENCE TO RELATED APPLICATIONS

This application claims priority to the U.S. provisional patent application Ser. No. 62/972,783, filed 62/972,783, filed Feb. 11, 2020, which is incorporated herein by reference in its entirety.

FIELD OF INVENTION

The present invention relates to a charging case for wireless earbuds, and more particularly, the present invention relates to a charging case that also sterilizes the wireless earbuds and an inner volume of the charging.

BACKGROUND

Wireless earbuds and charging cases of charging the wireless earbuds are known in the art. Such charging cases can be wired or wireless. The charging cases have an inbuilt battery for charging the earbuds, wherein a charging case itself also has to be charged. The charging cases generally have docks that can safely hold the earbuds and provide charging.

Earbuds are generally frequently touched by hands. Moreover, the earbuds may also be shared with another person. This makes the earbuds a carrier for microorganisms, and in particular a carrier of pathogenic microorganisms. Moreover, the soft cushion of the earbuds can easily harbor microorganisms and hasten their multiplication. A person touching the earbud may transfer the microbes from their hands to the earbuds which can then become a carrier for that microbe. Such microbes, including, fungi can cause ear infections as well.

Thus, a desire is there for a solution to the aforesaid problems. A desire is there for a device to sterilize the earbuds.

SUMMARY OF THE INVENTION

The following presents a simplified summary of one or more embodiments of the present invention in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a charging case for earbuds that can sterilize the ear buds.

It is another object of the present invention that the charging case promotes health and hygiene.

It is still another object of the present invention that the charging case can prioritize between the charging and sterilization.

It is yet another object of the present invention that the charging case is economical to manufacture.

It is a further object of the present invention that the charging case is compact and light in weight.

It is an additional object of the present invention that the charging case is portable.

In one aspect, disclosed is a charging case having one or more charging docks for charging the earbuds. The charging case can further have UV LEDs for automatically sterilizing the earbuds while charging.

These and other objects and advantages of the embodiments herein and the summary will become readily apparent from the following detailed description taken in conjunction with the accompanying drawings

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

Disclosed is a charging case for charging the earbuds that have UV LEDs for generating ultraviolet radiations in the far UV-C region to irradiating the inner volume of the charging case. The ultraviolet radiation can be within the UV-C range that is known to have disinfecting or microbiocidal action. It is to be understood that any radiations known for use in sterilization can be used, without departing from the scope of the present invention. The UV LEDs can be lit for a predefined duration which is at least the duration the microorganisms have to exposed to reduce the microbial load by at least 99.9 percent.

Figure 1:
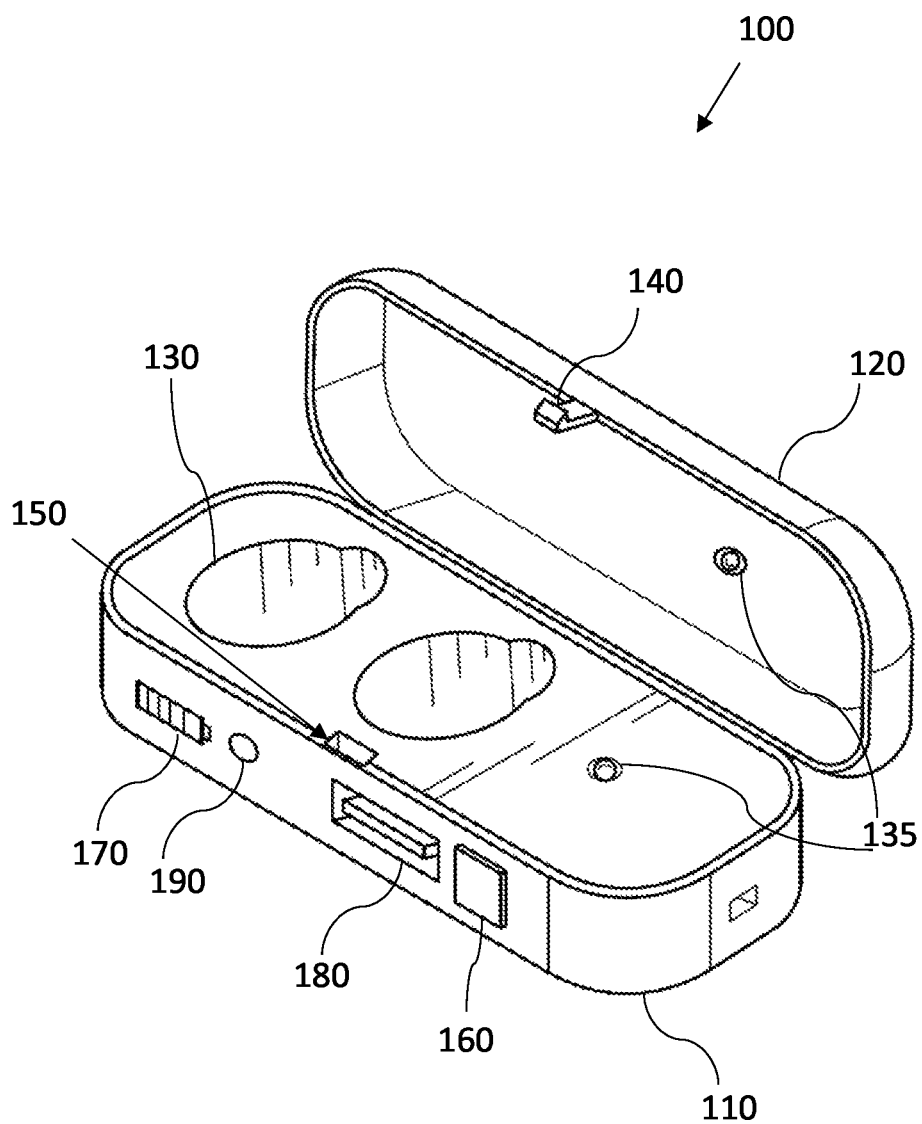
FIG. 1 shows a charging case for earbuds having UV LEDs, according to an exemplary embodiment of the present invention.

Referring to FIG. 1 which shows an exemplary embodiment of the charging case 100 having a box body 110 and a cover 120, the cover 120 coupled to the box body 110 through a hinge joint. The box body 110 having two charging docks 130 to which the earbuds can be mounted for charging. Besides the charging docks can be seen three UV LEDs 135 positioned to irradiate the docked earbuds. It is to be understood that that the position of the earbuds and UV LED's and their location can be varied based on the shape and size of the charging case.

Figure 2:
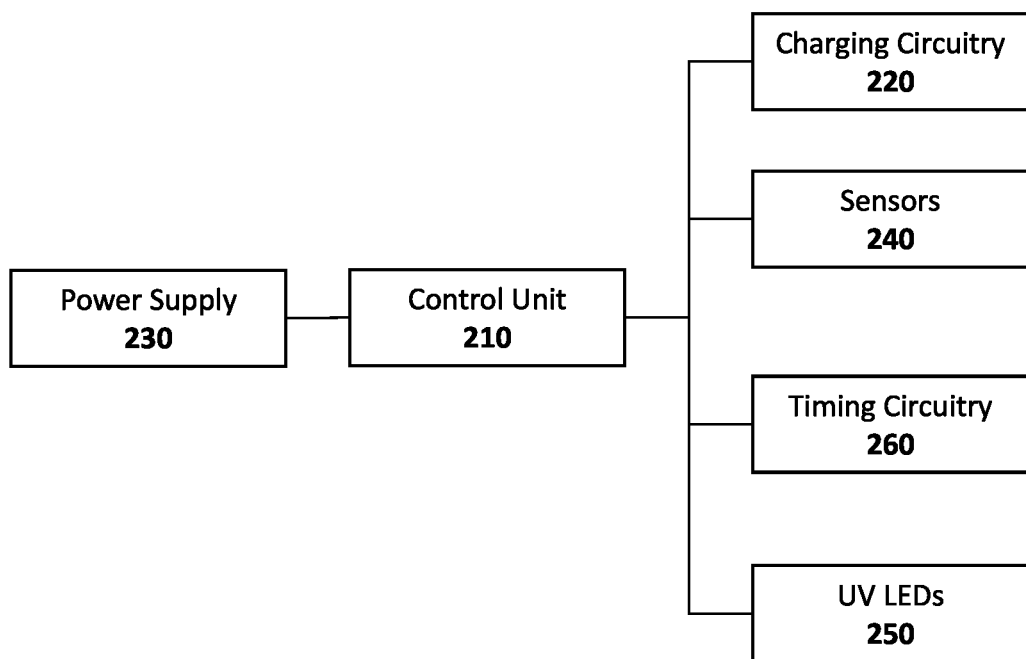
FIG. 2 is a block diagram showing an exemplary embodiment of the charging case, according to the present invention.

The cover having a hook 140 that can be engaged to lock member 150. The charging case 100 can have a sensor that detects the presence of earbuds in the charging docks 130. The charging case can also have a sensor that can detect the closing and opening of cover 120. The charging case can have a control unit, as shown in FIG. 2. The control unit 210 can be operably connected to the charging circuitry 220, sensors 240, timing circuitry 260, and UV LEDs 250. The charging circuitry can provide for the charging of the earbuds. Moreover, the charging circuitry 220 can be regulated by the control unit 210. The components of the charging case including the control unit can be powered by the power supply 230.

The power supply 230 can be a rechargeable battery, such as a Lithium-ion battery. The battery of the charging case 100 can be powered through a wired connection with a wall charger. A suitable charging interface, such as a USB port or USB-C Type port or any other known input/out port (not shown) can be provided for connecting to a wired charger, this same interface can be used to supply the power to the battery of the case and also draw the power from battery of the case to charge external devices. Alternately, the disclosed charging case can also be charged wirelessly. It is to be understood that the charging case can include both the option of wired and wireless charging of the battery of the charging case. The control unit can regulate the power supply to different components of the charging case.

The charging case 100 can have one or more UV LEDs 135 for irradiating the inner volume of the charging case 100. The inner surface of the charging case can have a reflective coating to enhance the sterilizing efficiency of the UV radiations. The UV radiations can sterilize the earbuds placed in the charging case 100. The control unit can sense the placing of the earbuds in the charging docks through the sensors. The control unit can also detect the closing of the cover of the charging case through a sensor. For example, a sensor can detect engaging of the hook 140 to the lock member 150. The sensor can be provided in the lock member 150. The control unit upon sensing the earbuds and the closing of the cover can automatically turn on the power supply to the UV LEDs, which can irradiate the inner surface of the charging case including the earbuds. The control unit upon sensing the closing of the cover can automatically turn on the power supply to the UV LEDs, which can irradiate/ sterilize the inner surface of the empty charging case itself. Thus, the user when removes the ear buds from the charging case and closed the cover, the charging case sterilize its inner volume. The UV LEDs can be strategically placed so that the earbuds can be sterilized uniformly. The charging docks 130 can also include UV LEDs to enhance the sterilization. FIG. 1 shows one UV LED in the box body and the other UV LED on the cover.

The control unit can have a timing circuitry that can be pre-set with a duration. The duration can be the duration for which the UV LEDs must be on. The control unit can turn the UV LEDs on for the pre-set duration and automatically shut them. The duration can be modified or reset later. The control unit can also detect the opening of the cover, and if the cover is opened while the UV LEDs are on, the control unit, for safety, can turn the UV LEDs off. The control unit can both charge the earbuds and the UV LEDs. The UV LEDs can be turned off after the predefined duration while the earbuds can continue to be charged.

In one case, both the UV LEDs and the charging circuitry can be powered by the same battery. The battery can have additional capacity for UV LEDs. The control unit can balance the charging of the earbuds and the LEDs. For example, in case the charge left in the batteries of the disclosed charging case is less, the control unit can stop the power supply to the UV LEDs and the earbuds can be charged. Thus, the control unit can optimize the power plan of the charging case, such as preference can be given to the charging of the earbuds.

In one exemplary embodiment, the disclosed charging case 100 also has an option of deep cycle sanitization. A separate button 160 can be provided on the outer side of the charging case 100, actuation of which causes the UV LEDs to remain on for more time than normal.

The disclosed charging case further includes one or more charging ports 180 for charging other electronic devices, such as a mobile phone. One or more charging ports can be integrated into a wall charging case. The charging port 180 can also be powered by the charging circuitry of the disclosed charging case 100.

A battery status indicator 170 can show the battery status as well as indicate the charging of the battery. The indicator 190 can show the status of UV lamps. The indicator 190 is off when the UV lamps are off. The indicator 190 can blink showing the warming of the UV lamps. A continuous blue indicator can show the normal operation of the UV lamp. While the red indicator can show the deep cycle operation of the UV lamps.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A charging case for earbuds comprising:
   a box body having a base, a front wall, and a rear wall defining an inner volume of the box body, top of the box body is open;
   a cover coupled to the box body, the cover configured to switch between an open state and a closed state,
   one or more charging docks in the box body for mounting one or more earbuds for charging,
   a plurality of UV LEDs, wherein at least one UV LED is disposed in the box body, and at least one UV LED is disposed in the cover, wherein the plurality of UV LEDs are configured to irradiate/sterilize an inner surface of the charging case uniformly, wherein the plurality of UV LEDs are also disposed within each of the one or more charging docks for uniformly irradiating the one or more earbuds, wherein an inner surface of the cover, the box body, and the one or more charging docks has a layer of reflective coating configured to enhance sterilizing efficiency of UV radiations;

a sensor for detecting the receiving of the one or more earbuds on the one or more charging docks, the sensor also configured to detect opening and closing of the cover; and a control unit operably coupled to the at least one UV LED, the sensor, and a charging circuitry, the charging circuitry configured to charge the one or more earbuds, the control unit configured to:
  receive a first signal from the sensor indicating the mounting of the at least one earbud on the at least one charging dock,
  receive a second signal from the sensor indicating the closing of the cover,
  upon receiving the first signal and the second signal, turning on the plurality of UV LEDs on for a predetermined duration,
  wherein the control unit further comprises a timing circuitry configured to receive a duration for which the plurality of UV LEDs are turned on.

2. The charging case according to claim 1, wherein the plurality of UV LEDs are configured to generate light in far UV-C region.

3. The charging case according to claim 1, wherein the charging case further comprises an integrated rechargeable battery, the control unit and the plurality of UV LEDs is powered by the integrated rechargeable battery.

4. The charging case according to claim 1, wherein the control unit is also configured to:
  receive a third signal from the sensor, the third signal indicative of opening of the cover, and
  upon receiving the third signal, while the plurality of UV LEDs is turned on, the control unit turns the plurality of UV LEDs off.

5. The charging case according to claim 1, wherein the charging case further comprises one or more charging port configured for charging an external electronic devices.

6. The charging case according to claim 1, wherein the control unit is further configured to:
  receive a third signal indicating the removal of at least one earbud of the one or more ear buds,
  upon receiving the third signal, receive a fourth signal indicating closing of the cover, and
  upon receiving the fourth signal, turning the plurality of UV LEDs on for the predetermined duration.

7. The charging case according to claim 1, wherein the control unit is configured to balance charging of the one or more earbuds and the plurality of UV LEDs, wherein the control unit is configured to prioritize the charging of the one or more ear buds over the plurality of UV LEDs.

8. The charging case according to claim 7, wherein the control unit is configured to provide for deep cycle sanitization which causes the plurality of UV LEDs to remain on for more time than normal.

* * * * *